(12) United States Patent
Porter

(10) Patent No.: US 9,289,745 B1
(45) Date of Patent: Mar. 22, 2016

(54) LIQUID PHASE ISOMERIZATION PROCESS

(71) Applicant: ExxonMobil Chemical Patents Inc., Baytown, TX (US)

(72) Inventor: John R. Porter, Friendswood, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 14/947,586

(22) Filed: Nov. 20, 2015

Related U.S. Application Data

(62) Division of application No. 13/861,473, filed on Apr. 12, 2013.

(60) Provisional application No. 61/625,418, filed on Apr. 17, 2012.

(51) Int. Cl.
*B01J 8/00* (2006.01)
*B01J 10/00* (2006.01)
*C07C 5/27* (2006.01)
*C07C 7/12* (2006.01)
*C07C 7/14* (2006.01)
*B01J 19/24* (2006.01)

(52) U.S. Cl.
CPC ............... *B01J 19/2445* (2013.01); *B01J 8/00* (2013.01); *B01J 2219/24* (2013.01)

(58) Field of Classification Search
CPC ............. C07C 5/27; C07C 7/12; C07C 7/14; B01J 8/00; B01J 10/00
USPC ........... 585/477, 478, 812, 825; 422/187, 188
See application file for complete search history.

(56) References Cited

U.S. PATENT DOCUMENTS

| | | |
|---|---|---|
| 3,813,452 A | 5/1974 | Bieser |
| 3,856,874 A | 12/1974 | Hayward |
| 4,118,429 A | 10/1978 | Fritsch et al. |
| 7,847,137 B2 * | 12/2010 | Negiz ................... C07C 6/123 585/319 |

* cited by examiner

*Primary Examiner* — Thuan D Dang

(57) ABSTRACT

Liquid phase isomerization technology is employed in a manner to increase efficiency and reduce energy in paraxylene recovery.

2 Claims, 1 Drawing Sheet

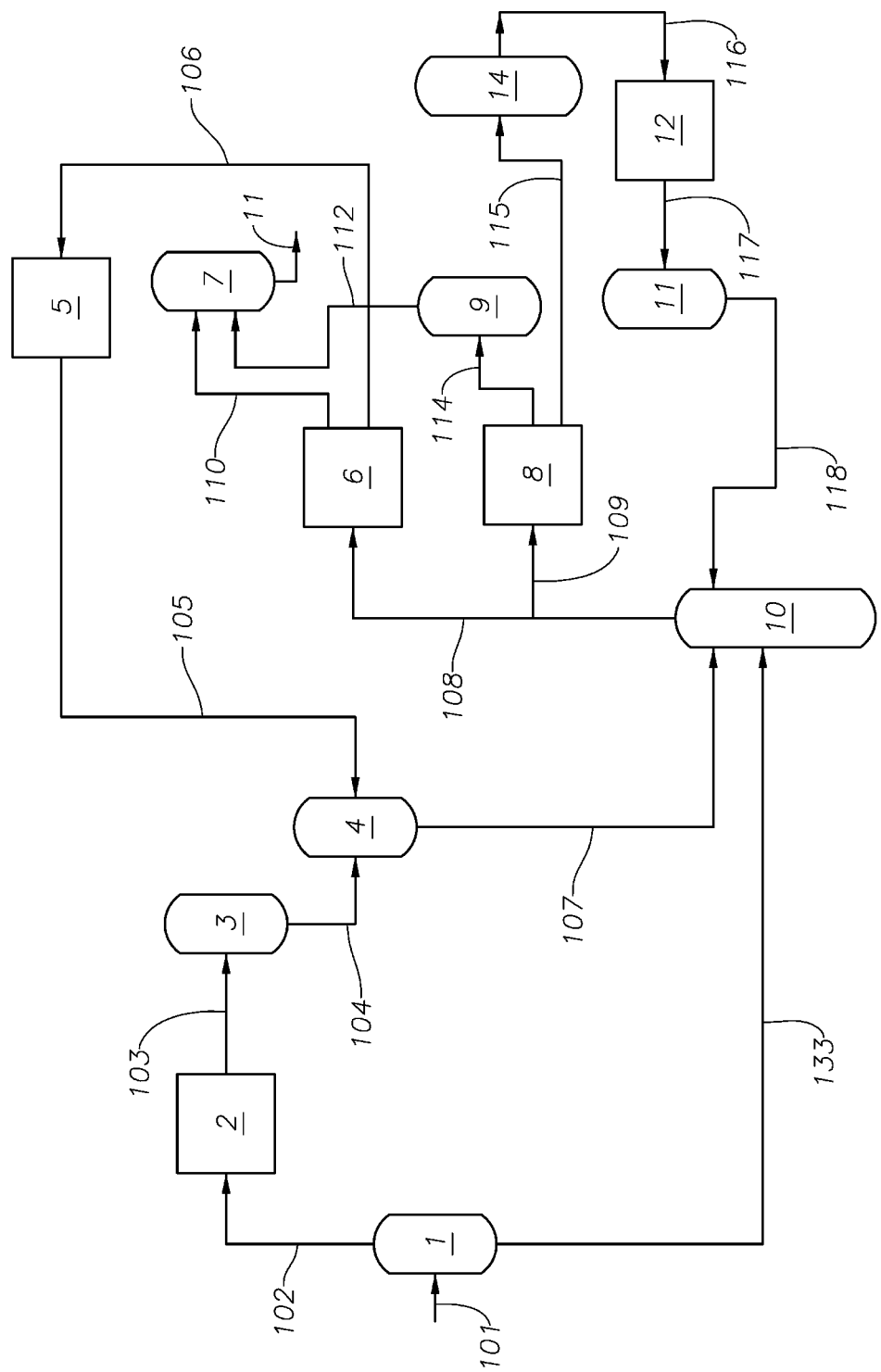

LIQUID PHASE ISOMERIZATION PROCESS

CROSS REFERENCE TO RELATED APPLICATIONS

This application is a divisional of and claims priority to and the benefit of U.S. patent application Ser. No. 13/861,473, filed Apr. 12, 2013, and U.S. Provisional Application No. 61/625,418, filed on Apr. 17, 2012, the disclosures of which are incorporated herein by reference in their entirety.

FIELD OF THE INVENTION

The invention relates to a process for liquid phase isomerization and a system adapted for said process.

BACKGROUND OF THE INVENTION

Ethylbenzene (EB), para-xylene (PX), ortho-xylene (OX) and meta-xylene (MX) are present together in many C8 aromatic product streams from chemical plants and oil refineries. While all these species have important uses, market demand for paraxylene, used extensively as starting material for making synthetic fibers, is greater than for the other C8 aromatic isomers.

Given the higher demand for PX as compared with its other isomers, there is significant commercial interest in maximizing PX production from any given source of C8 aromatic materials. However, there are two major technical challenges in achieving this goal of maximizing PX yield. First, the four C8 aromatic compounds, particularly the three xylene isomers, are usually present in concentrations dictated by the thermodynamics of production of the C8 aromatic stream in a particular plant or refinery. As a result, the PX production is typically limited to the amount originally present in the C8 aromatic stream, which is, again in the typical case, approximately 24 mol % at thermal equilibrium, unless additional processing steps are used to increase the amount of PX and/or to improve the PX recovery efficiency. (Methods of making paraxylene with higher selectivity, such as by toluene alkylation with methanol, are well-known.) Secondly, the C8 aromatics are difficult to separate due to their similar chemical structures and physical properties and identical molecular weights.

A variety of methods are known to increase the concentration of PX in a C8 aromatics stream. These methods normally involve a loop system comprising a separation step, in which at least part of the PX is recovered (and removed from the system in a PX-enriched stream), leaving a PX-depleted stream, the latter being sent to a xylene isomerization step, in which the PX content of the PX-depleted stream is returned back towards thermal equilibrium concentration and recycled to the separation step.

The separation step is typically accomplished using fractional crystallization techniques, which is based on the difference on the freezing points of the C8 aromatic isomers, or adsorption separation techniques, which is based on the selectivity of adsorbant for one isomer over another. Amongst the well-known adsorption separation techniques are the UOP Parex™ Process and the IFP Eluxyl™ Process.

A prior art system including the separation step and isomerization steps referred to above generally will include the use of numerous fractionation towers, e.g., a reformate splitter, a benzene recovery tower, a toluene recovery tower, a xylene rerun tower, an isomerization unit heptanizer, and one or more towers associated with the adsorption separation unit, e.g., Parex™ adsorptive separation unit(s). A system comprising a Parex™ adsorptive separation unit using PDEB (para-diethylbenzene) as a desorbent ("heavy" Parex™ adsorptive separation unit) will have an extract tower, raffinate tower(s) and finishing tower(s) while a system comprising a Parex™ adsorptive separation unit using toluene as a desorbent ("light" Parex™ adsorptive separation unit) only needs the extract and raffinate towers, since the extract tower separates out both the toluene in the desorbent stream as well as trace toluene in the xylene feed. In a plant using both types of units the light extract tower can serve as the finishing tower for the heavy unit.

The isomerization step typically is accomplished by contact with a molecular sieve catalyst, such as ZSM-5, under appropriate conditions to convert a para-xylene-depleted mixture of C8 aromatic hydrocarbons to thermodynamic equilibrium amounts. Historically xylene isomerization has been accomplished in the vapor phase, however recently liquid isomerization units have found increasing use in para-xylene separation systems.

It is known that liquid phase isomerization technology can reduce energy usage in an aromatics plant by reducing the amount of feed to vapor phase isomerization. Vapor phase isomerization requires more energy due to the phase change in the isomerization process. In addition, vapor phase isomerization requires more fractionation energy in the isomerization system's heptanizer and xylene rerun tower.

It is known in the prior art to integrate a liquid isomerization unit with a vapor phase isomerization unit by taking a slip stream from the para-depleted mixed xylenes product of a raffinate tower downstream of a paraxylene recovery unit (whether it is Eluxyl™ unit, Parex™ adsorptive separation unit, or light and heavy Parex™ adsorptive separation unit in parallel), and then passing the para-depleted mixed xylenes through the liquid phase isomerization unit to provide an equilibrium mixture of xylenes, which is then recycled back to the paraxylene recovery unit(s). Thus, the liquid phase isomerization unit is used essentially to supplement the vapor phase isomerization unit, but otherwise the processing in the xylenes loop is the same.

The present inventor has realized that the raffinate from the paraxylene recovery unit may be sent directly to the liquid isomerization unit without one or more intervening fractionation towers. Thus, in the integration of liquid phase isomerization and adsorptive separation there does not need to be a raffinate tower as used in conventional paraxylene recovery systems.

SUMMARY OF THE INVENTION

The invention is directed to a process comprising liquid isomerization for improved paraxylene recovery and a system adapted therefore. In embodiments the process is integrated with at least one of a light Parex™ adsorptive separation unit and optionally a heavy Parex™ adsorptive separation unit. In embodiments a raffinate stream from one or both of said units is processed through the liquid phase isomerization process, without an intervening fractionation tower (i.e., raffinate tower in conventional systems), and then the product of the liquid phase isomerization unit, a stream having a thermodynamic equilibrium concentration of xylenes, may be fractionated with other C7 and C8 aromatic hydrocarbon-containing streams, thus, avoiding at least one fractionation tower in the system.

In embodiments the bottom stream from a benzene tower and the raffinate stream from the liquid phase isomerization unit are fed to separate points in the same tower.

In embodiments the improvement comprises the combination in series of a xylene separation step and a liquid isomerization step without an intervening step of fractionation between the separation and isomerization steps, and in a further improvement, with the product stream of the liquid isomerization stream passed to a tower used for fractionation of toluene and xylenes. It is preferred that in the case of the use of a Parex™ adsorptive separation unit that PDEB is not used as the desorbent, as the liquid phase isomerization unit typically will isomerize PDEB. Thus, it is preferred that the desorbent in the stream sent to the liquid phase isomerization unit be toluene or some other desorbent suitable for adsorptive separation of the species of interest that is not isomerized by liquid phase isomerization to an extent that it would build up the system to a significant extent, which can be determined by routine experimentation.

It is an object of the invention to provide a liquid phase isomerization of a paraxylene-depleted C8 aromatic hydrocarbon stream from a paraxylene separation unit such as an adsorption unit (e.g., Parex™ unit) integrated with a toluene product fractionation to avoid at least one tower in a xylenes plant.

It is also an object of the invention to achieve a thermodynamic synergy and thus energy efficiency by coupling liquid phase isomerization directly, without intervening fractionation, to a liquid phase isomerization unit, and also to more fully integrate a xylenes plant by coupling a toluene/xylenes tower, liquid phase isomerization unit, and Parex™ unit in series, without additional towers.

These and other objects, features, and advantages will become apparent as reference is made to the following detailed description, preferred embodiments, examples, and appended claims.

BRIEF DESCRIPTION OF THE DRAWINGS

FIG. 1 is a schematic illustration of one possible configuration of a Parex™ unit operating with a liquid isomerization unit according to the present invention.

DETAILED DESCRIPTION

According to the invention, liquid phase isomerization technology is employed in a manner to increase efficiency and reduce energy in paraxylene recovery. In order to better understand the invention reference is made to the accompanying FIG. 1, which is a schematic illustration of an embodiment of the invention and should not be taken as limiting thereof.

In one embodiment, there is a process for the production of paraxylene from a feedstream comprising a mixture of C8 aromatic hydrocarbons, comprising a xylene separation step, including the separation of paraxylene from its C8 aromatic isomers to provide a paraxylene-enriched stream and a paraxylene-depleted stream, and a liquid-phase isomerization step, including the isomerization of said paraxylene-depleted stream to produce an equilibrium xylenes stream, the improvement characterized in that the paraxylene-depleted stream is used directly as feed to said liquid-phase isomerization step, without intervening separation step.

In another embodiment, there is a process for the production of paraxylene from a feedstream comprising a mixture of C8 aromatic hydrocarbons, comprising:
(a) separation of said feedstream into a first product enriched in C8+ species relative to said feedstream and a second product enriched in C7− aromatic species relative to said feedstream;
(b) passing said first product to a fractionation tower to provide a third product enriched in xylenes relative to said first product and a fourth product depleted in xylenes relative to said first product;
(c) passing the third product to a xylene separation step to provide a product enriched in paraxylene when compared with said third product, and a raffinate product, characterized as depleted of paraxylene when compared with said third product; and
(d) passing said raffinate directly, without a fractionation step, to a liquid phase isomerization unit, to provide a product enriched in paraxylene when compared with said raffinate.

The invention may be better understood by reference to a specific embodiment, which is not to be taken as limiting of the present invention.

FIG. 1 illustrates the embodiment wherein the paraxylene recovery system includes both a light Parex™ adsorptive separation unit 6, using toluene as desorbent, and heavy Parex™ unit 8, using PDEB as adsorbent. The raffinate stream 106 (comprising toluene and paraxylene-depleted xylenes) from the light Parex™ adsorptive separation unit 6 is routed through the liquid phase isomerization unit 5 to isomerize the para-xylene depleted raffinate stream in line 106 to equilibrium. The toluene portion in this stream 106 passes through unreacted in the liquid isomerization process and the stream 105 passing out of the isomerization unit 5 can be fractionated in toluene tower 4 along with other toluene/xylene streams, such as the stream 104 from the bottom of the benzene tower 3. In addition to saving the capital cost, operational costs, maintenance cost, and the like, of one or more fractionation towers, there is a thermodynamic synergy that will result in energy savings when the bottom stream 104 from the benzene tower 4 and the light Parex™ adsorptive separation unit 6 raffinate stream 106, isomerized in unit 5, are fed to separate feed points in the same tower 4. The bottom stream 107 from the toluene tower 4 is advantageously reprocessed through the xylene rerun tower 10. However, since this stream typically has only trace aromatic C9+ species, the stream can be fed very high in the xylene rerun tower 10 and therefore the impact on xylene rerun tower 10 energy is minimal.

The additional elements of the embodiment described schematically by the system shown in FIG. 1 include the feed 101, typically a reformate feed, introduced into separation unit 1, such as a fractionation tower, to provide an overhead 102 comprising benzene, toluene, and non-aromatics, and a bottoms product 133, comprising xylenes and heavier species (e.g., C9+ aromatics), sent to xylene rerun tower 10 described above, which provides the feed to the paraxylene separation unit, here light Parex™ adsorptive separation unit 6 and heavy Parex™ adsorptive separation unit 8, via conduits 108 and 109, respectively. The overhead 102 from unit 1 is introduced to an aromatics extraction unit 2, per se known in the art, to provide an extract 103 comprising benzene and toluene, which are separated, successively, in benzene tower 3 fluidly connected through conduit 104 to toluene tower 4, described previously.

In FIG. 1, downstream of the light Parex™ adsorptive separation unit 6, conduit 110 provides the extract containing desired product to the light extract tower 7, wherein paraxylene is typically taken as a bottoms product 11. Similarly, downstream of heavy Parex™ adsorptive separation unit 8 conduit 114 provides extract to the heavy extract tower 9 and overhead product is sent via 112 to extract tower 7, described above. The paraxylene product from the heavy extract tower 9 is the overhead product 112. The overhead product 112 has a small amount of toluene and it is sent to the light extract tower 7. The bottoms product from the light extract tower 7 is then the combined paraxylene product from the light and heavy Parex™ unit. Raffinate 115 from the heavy Parex™ adsorptive separation unit 8 is sent to raffinate tower 14, wherein PDEB is separated from other species to yield a paraxylene-depleted stream 116, isomerized in unit 12 (which may be liquid or vapor phase isomerization). Deheptanizer 11 is typically one of the possible fractionation towers between the xylene rerun tower 10 and isomerization unit 12, fluidly connected, respectively, by conduits 118 and 117.

One of ordinary skill in the art in possession of the present disclosure will appreciate that not all possible feeds and products to and from the various units nor fluid connections between the units shown (nor other possible units which may be present in a xylenes plant) are shown in FIG. 1, and likewise valves and the like are also not shown for convenience of view. One of ordinary skill in the art, in possession of the present disclosure, would also be able to determine operating conditions of the various units described herein without more than routine experimentation.

It has also been surprisingly discovered that the presence of low concentrations of cumene (such as 300 ppm by weight) in a xylenes feed mixture used in the liquid phase xylenes isomerization will result in a fast deactivation of the catalyst employed and also that the same liquid phase xylenes isomerization catalyst recovered its initial activity when a cumene-free (less than about 25 ppm by weight) xylenes mixture is used as feed, after such deactivation due to the use of a xylene mixture contaminated with low concentrations of cumene.

This is shown by the following experimental results, which should not be taken as limiting of the invention claimed hereinbelow. The liquid phase isomerization reaction was carried out in a fixed bed up-flow reactor using a catalyst comprising H-ZSM-5 extrudates. The reaction using xylenes saturated with $H_2$ was carried out within a temperature range between 246-255° C. and the weight hourly space velocity (WHSV) between about 2 and 4. The reactor effluent was analyzed by an online Gas Chromatograph (GC) equipped with a DB-WAX 60 m (i.d. 0.25 mm, Agilent Technologies) column, allowing the determination of the products yields. The reaction is run under approach to equilibrium conditions (95+% approach to equilibrium) and the aim is to maximize p-xylene yield under the above mentioned conditions.

By monitoring paraxylene (PX) yield as a function of time on stream by GC, it is observed that there is a rapid decrease in PX yield when the catalyst is exposed to a cumene contaminated xylene feed, containing about 300 ppm by wt. of cumene and then an increase in PX yield when an essential cumene free xylene mixture (less than 25 wt ppm cumene) is charged.

The invention has been described above with reference to numerous embodiments and specific examples. Many variations will suggest themselves to those skilled in this art in light of the above detailed description. All such obvious variations are within the full intended scope of the appended claims.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. An apparatus adapted for production of paraxylene comprising:
   a separation unit that separates a feedstream comprising a mixture of C8 aromatic hydrocarbons into a first product enriched in C8+ species relative to said feedstream and a second product enriched in C7− aromatic species relative to said feedstream;
   a fractionation tower that fractionates said first product to provide a third product enriched in xylenes relative to said first product and a fourth product depleted in xylenes relative to said first product;
   a xylene separation section that separates the third product to provide a product enriched in paraxylene when compared with said third product, and a raffinate product, characterized as depleted of paraxylene when compared with said third product;
   a liquid phase isomerization unit that accepts said raffinate product to provide a product enriched in paraxylene when compared with said raffinate;
   wherein said xylene separation section includes at least two adsorptive separation units;
   wherein the first of said adsorptive separation units is a light adsorptive separation unit that uses toluene as a desorbent and is fluidly connected in series to said liquid phase isomerization unit, with no intervening fractionation tower; and
   wherein the second of said adsorptive separation units is a heavy adsorptive separation unit that uses para-ethylbenzene as a desorbent and is fluidly connected in series to a fractionation tower and a vapor phase isomerization unit.

2. The apparatus of claim 1, wherein the liquid phase isomerization unit and vapor phase isomerization unit are in parallel.

\* \* \* \* \*